United States Patent
Cyran

(10) Patent No.: US 10,630,756 B2
(45) Date of Patent: Apr. 21, 2020

(54) SYSTEM AND METHOD FOR AUTOMATICALLY DOWNLOADING DATA SUCH AS SLEEP STUDY DATA

(71) Applicant: KONINKLIJKE PHILIPS N.V., Eindhoven (NL)

(72) Inventor: Robert John Cyran, Delmont, PA (US)

(73) Assignee: KONINKLIJKE PHILIPS N.V., Eidhoven (NL)

( * ) Notice: Subject to any disclaimer, the term of this patent is extended or adjusted under 35 U.S.C. 154(b) by 799 days.

(21) Appl. No.: 14/890,193

(22) PCT Filed: May 28, 2014

(86) PCT No.: PCT/IB2014/061769
§ 371 (c)(1),
(2) Date: Nov. 10, 2015

(87) PCT Pub. No.: WO2014/191927
PCT Pub. Date: Dec. 4, 2014

(65) Prior Publication Data
US 2016/0127505 A1    May 5, 2016

Related U.S. Application Data

(60) Provisional application No. 61/829,306, filed on May 31, 2013.

(51) Int. Cl.
H04L 29/08    (2006.01)
G06F 16/903    (2019.01)
(Continued)

(52) U.S. Cl.
CPC ........ *H04L 67/06* (2013.01); *G06F 16/90335* (2019.01); *G16H 10/60* (2018.01);
(Continued)

(58) Field of Classification Search
CPC ......... H04L 67/06; H04L 67/34; H04L 67/42; H04L 67/1095; G06F 17/30979; G06F 19/322; G16H 10/60
(Continued)

(56) References Cited

U.S. PATENT DOCUMENTS 6,195,678 B1    2/2001    Komuro
6,842,770 B1    1/2005    Serlet et al.
(Continued)

FOREIGN PATENT DOCUMENTS

CN    101093468 A    12/2007
CN    102711062 A    10/2012
(Continued)

OTHER PUBLICATIONS

U.S. Appl. No. 61/751,698, filed Jan. 2013, US, Vibhor et al.*
(Continued)

*Primary Examiner* — James E Springer

(57) ABSTRACT

A method of automatically downloading data, the method including periodically querying a server (32) for sets of data meeting predetermined criteria, receiving information on any sets of data meeting the predetermined criteria, for each set of data meeting the predetermined criteria, determining if the set of data exists or is up to date locally, and upon determining that a selected set of data does not exist or is not up to date locally, downloading at least a portion of the selected set of data.

13 Claims, 3 Drawing Sheets

(51) Int. Cl.
*G16H 10/60* (2018.01)
*H04L 29/06* (2006.01)

(52) U.S. Cl.
CPC .......... *H04L 67/1095* (2013.01); *H04L 67/34* (2013.01); *H04L 67/42* (2013.01)

(58) Field of Classification Search
USPC ........................................................ 709/219
See application file for complete search history.

(56) References Cited

U.S. PATENT DOCUMENTS

| | | | | |
|---|---|---|---|---|
| 7,282,027 | B2* | 10/2007 | Sotos | A61B 5/0002 |
| | | | | 128/920 |
| 9,906,583 | B2* | 2/2018 | Cyran | G16H 10/60 |
| 2002/0120310 | A1* | 8/2002 | Linden | G06F 19/3418 |
| | | | | 607/60 |
| 2004/0068724 | A1 | 4/2004 | Gardner, III et al. | |
| 2004/0244807 | A1* | 12/2004 | Sun | A61B 5/0002 |
| | | | | 600/26 |
| 2005/0042589 | A1* | 2/2005 | Hatlestad | A61B 5/0031 |
| | | | | 434/262 |
| 2008/0220403 | A1* | 9/2008 | Marling | G16H 40/63 |
| | | | | 434/262 |
| 2008/0243014 | A1* | 10/2008 | Moussavi | A61B 5/087 |
| | | | | 600/529 |
| 2008/0279212 | A1 | 11/2008 | Tominaga | |
| 2011/0252125 | A1* | 10/2011 | Tse | G06F 17/30174 |
| | | | | 709/224 |
| 2014/0201141 | A1* | 7/2014 | Vibhor | H04L 29/0854 |
| | | | | 707/622 |
| 2014/0213913 | A1* | 7/2014 | Parfenova | A61B 5/4818 |
| | | | | 600/484 |
| 2016/0270719 | A1* | 9/2016 | Liu | G16H 50/30 |

FOREIGN PATENT DOCUMENTS

| | | |
|---|---|---|
| JP | H10133881 A | 5/1998 |
| JP | 2003157197 A | 5/2003 |
| JP | 2004344265 A | 12/2004 |
| JP | 2009104638 A | 5/2009 |
| JP | 2012123693 A | 6/2012 |

OTHER PUBLICATIONS

Trapani, Gina, Free Ways to Synchronize Folders Between Computers, Mar. 26, 2008, https://lifehacker.com/free-ways-to-synchronize-folders-between-computers-372175 (Year: 2008).*

* cited by examiner

SYSTEM AND METHOD FOR AUTOMATICALLY DOWNLOADING DATA SUCH AS SLEEP STUDY DATA

CROSS-REFERENCE TO PRIOR APPLICATIONS

This application is the U.S. National Phase application under 35 U.S.C. § 371 of International Application Serial No. PCT/IB2014/061769, filed on May 28, 2014, which claims the benefit of U.S. Application Ser. No. 61/829,306, filed on May 31, 2013. These applications are hereby incorporated by reference herein.

BACKGROUND OF THE INVENTION

1. Field of the Invention

The present invention pertains to downloading data, and, in particular, to a system and method for automatically downloading sleep study data.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Various methods have been used to assess whether a patient suffers from OSA. The most comprehensive method is a clinical polysomnogram (PSG), which can diagnose many significant sleep pathologies. A PSG generally involves a sleep study of a patient where audio and other parameters of the patient is recorded while the patient sleeps. A technician then "scores" the recorded data. Scoring the recorded data involves analyzing the data to identify events that occurred during the PSG that may be useful in diagnosing sleep pathologies. Data collected during a PSG is generally stored in several different files such as multiple audio files, other data files, and a scoring file.

The PSG data (also referred to as sleep study data) is generated or used in several different locations, such as a sleep lab, a scoring technician's office, and a physician's office. It is preferable to store the PSG at a central location, such as a server, where it is accessible to multiple locations through a network, such as the internet.

The PSG data is generated and updated at several locations, which necessitates transferring and updating files between the remote locations and the central location to ensure that the PSG data being accessed by a user is up to date. A file transfer protocol (FTP) server on a server at the central location has been used to download PSG data from the central location to the remote locations. Other file sharing systems have also been used to manage file transfers between the central location and the remote locations. However, these file transfer mechanisms are initiated in an on-demand fashion. That is, when a user wants to access PSG data, the user manually initiates a download of the PSG data from the server and once the download is complete, the user accesses the PSG data at the remote location.

The amount of PSG data can become quite large and in many cases can exceed one gigabyte. Thus, a user could end up waiting a substantially amount of time for the PSG data to download before he is able to access it.

Accordingly, a need exists for improvement in downloading PSG data files from a central location to a remote location.

SUMMARY OF THE INVENTION

In one embodiment, a method of automatically downloading data includes periodically querying a server for sets of data meeting predetermined criteria, receiving information on any sets of data meeting the predetermined criteria, for each set of data meeting the predetermined criteria, determining if the set of data exists or is up to date locally, and upon determining that a selected set of data does not exist or is not up to date locally, downloading at least a portion of the selected set of data.

In another embodiment, a non-transitory computer readable medium storing one or more programs, including instructions, which when executed by a computer, causes the computer to perform a method of automatically downloading data, the method including periodically querying a server for sets of data meeting predetermined criteria, receiving information on any sets of data meeting the predetermined criteria, for each set of data meeting the predetermined criteria, determining if the set of data exists or is up to date locally, and upon determining that a selected set of data does not exist or is not up to date locally, downloading at least a portion of the selected set of data.

In another embodiment, a system to automatically download data includes a client device structured to periodically query a server for sets of data meeting predetermined criteria, to receive information on any sets of data meeting the predetermined criteria, and, for each set of data meeting the predetermined criteria, to determine if the set of data exists or is up to date locally for each set of data meeting the predetermined criteria, determining if the set of data exists or is up to date locally, wherein the client device is structured to download at least a portion of a selected set of data upon determining that the selected set of data does not exist or is not up to date locally.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
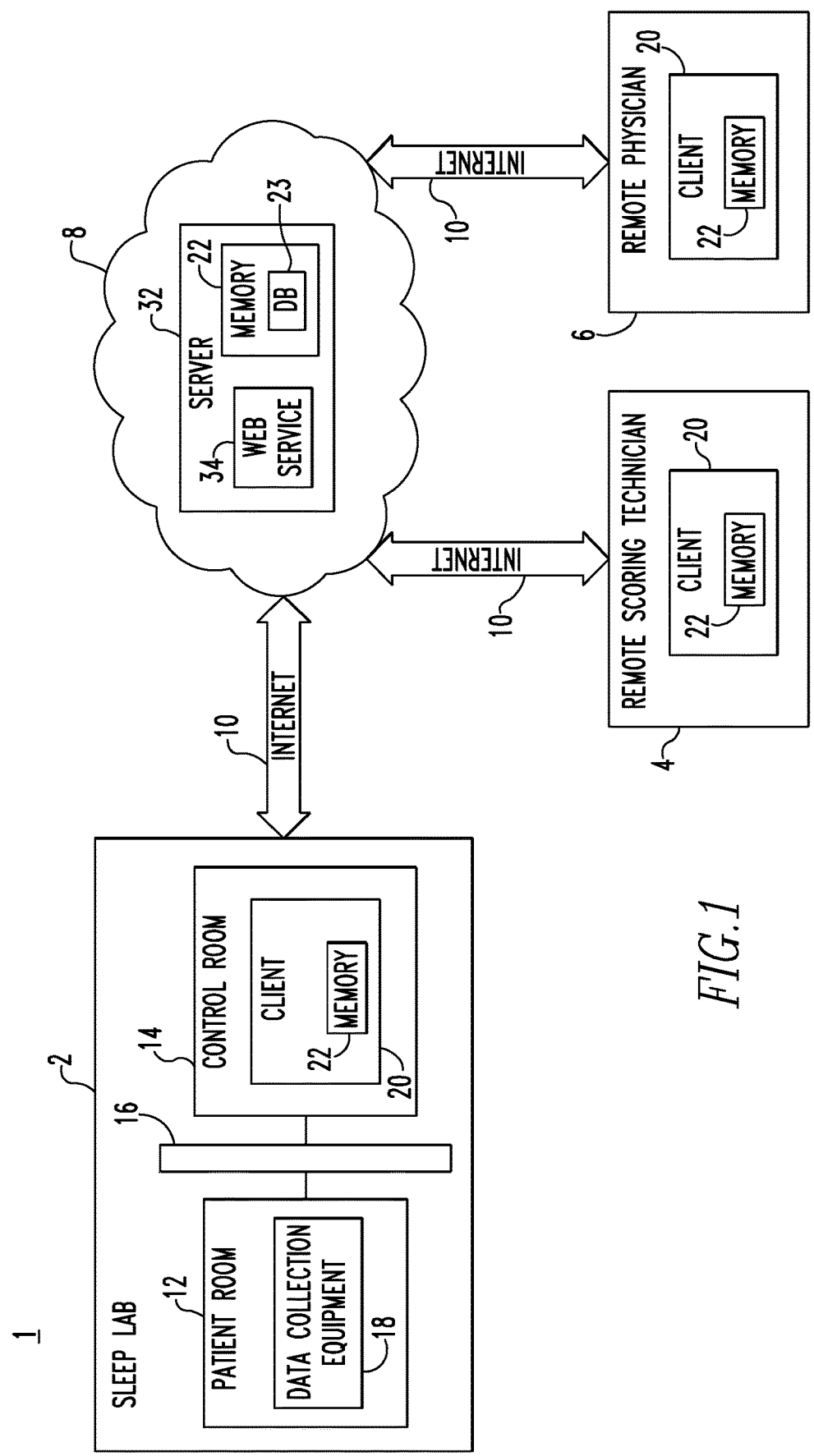
FIG. 1 is a schematic view of a system adapted to collect and store sleep study data in a centralized location according to one exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 1 adapted to collect and store sleep study data is generally shown in FIG. 1. System 1 is distributed over several locations including a sleep lab 2, a remote scoring technician site 4, a remote physician site 6, and a central server site 8. Central server site 8 includes a server 32 and each of sleep lab 2, remote scoring technician site 4, and remote physician site 6 include a client 20. Clients 20 are each communicatively connected to server 32 by suitable network connections such as internet connections 10.

Clients 20 are any suitable processing device such as, without limitation, a general-purpose computer, a wireless device, a personal computer, or a mobile phone. Clients 20 and server 32 each include an associated memory 22. Memory 22 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 22 may also be located outside of clients 20 or server 32 and communicatively connected with its associated client 20 or server 32. Memory 22 may also be a removable device that is able to be removed from its associated client 20 or server 32.

Sleep lab 2 includes a patient room 12 and a control room 14. Patient room 12 and control room 14 are communicatively connected by a suitable network connection such as a local area network connection 16. Patient room 12 includes data collection equipment 18. Data collection equipment 18 is used to collect raw sleep study data such, without limitation, audio and video data, electroencephalogram (EEG) data, electrocardiogram (ECG) data, electroculogram (EOG) data, electromyogram (EMG) data, measurements of nasal airflow, measurements of blood oxygen levels and/or other physiological parameters. Control room 14 includes client 20 and memory 22. The raw sleep study data is transferred from data collection equipment 18 to client 20 via local area network connection 16 and is stored in memory 22. The raw sleep study data is stored in memory 22 as a set of files.

Remote scoring technician site 4 includes its associated client 20 and memory 22. A scoring technician at remote scoring technician site 4 "scores" raw sleep study data and stores the scoring data in memory 22 as a file. The scoring data includes data such as, without limitation, sleep staging data, apnea event data, and high heart rate event data.

Remote physician site 6 includes its associated client 20 and memory 22. A physician at remote physician site 6 reviews the raw sleep study data and scoring data in order to diagnose a patient.

Central server site 8 includes server 32 which is communicatively connected with clients 20 in order to send or receive data. Server 32 includes memory 22 including a database 23 which stores the data. Server 32 also includes web service 34. Web service 34 coordinates communication between server 32 and clients 20 such as responding to requests from clients 20 for data uploads or downloads. Server 32 is structured to centrally store sleep study data where it can be downloaded or updated by any of clients 20.

Although sleep lab 2, remote scoring technician site 4 and remote physician site 6 are shown in FIG. 1, it will be appreciated that any suitable remote sites may be adapted to access sleep study data at central server site 8 without departing from the scope of the disclosed concept.

Figure 2:
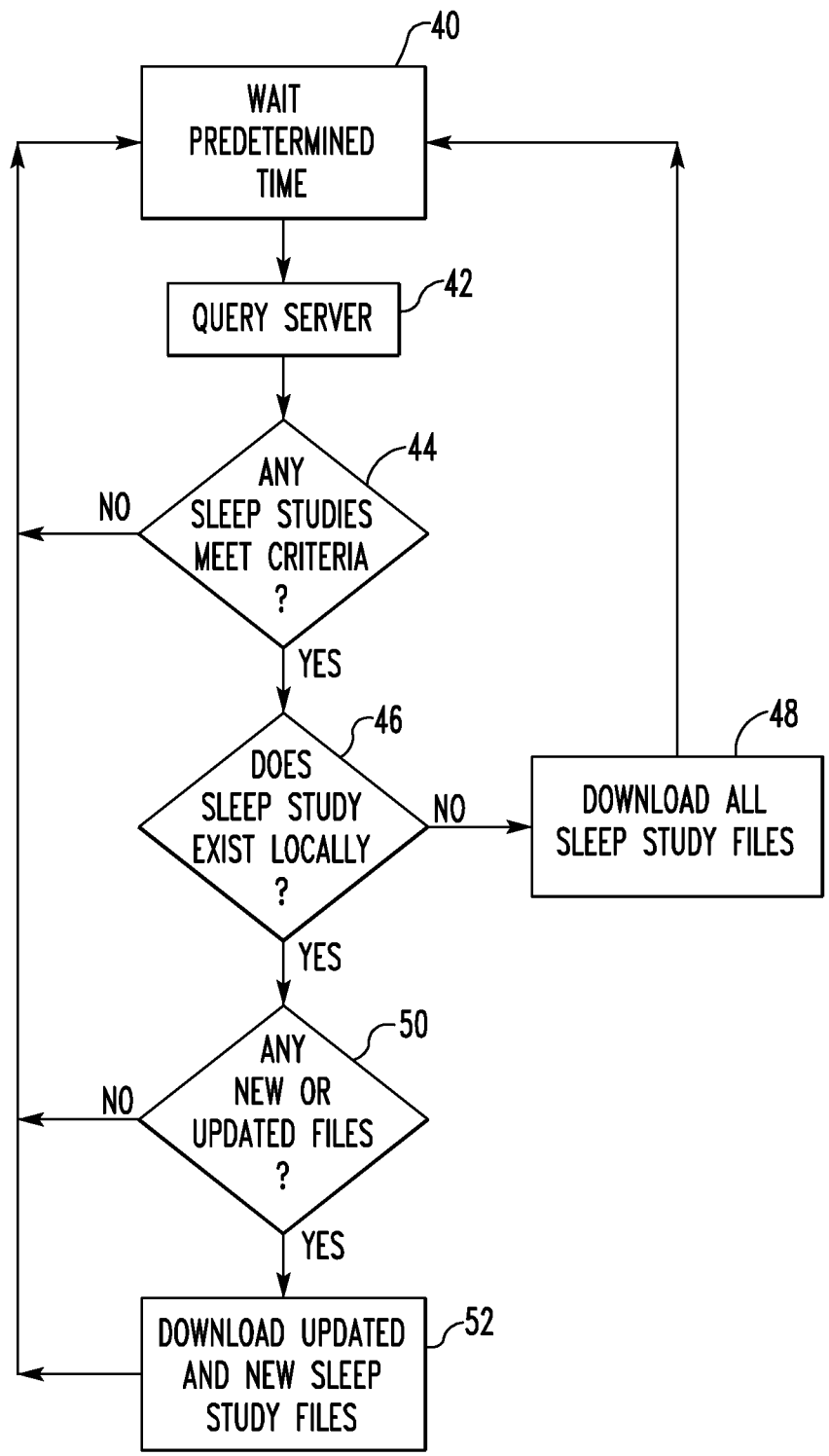
FIG. 2 is a flowchart of a method of automatically downloading sleep study files according to one exemplary embodiment of the disclosed concept.

A flowchart of a method of automatically downloading sleep study files from server 32 to client 20 in accordance with an exemplary embodiment of the disclosed concept is shown in FIG. 2. Generally, the method of FIG. 2 is executed by client 20 to automatically initiate downloads of sleep studies meeting predetermined criteria. In more detail, at 40 client waits a predetermined time. The predetermined time may be, without limitation, one minute. However, it will be appreciated that the predetermined time may be any suitable amount of time.

After the predetermined amount of time has passed, client 20 queries server 32 at 42. The query to the server 32 includes predetermined criteria. Server 32 checks database 23 for any sleep studies stored at the server 32 meeting the predetermined criteria provided by client 20. The predetermined criteria may include, for example and without limitation, a user the sleep study is assigned to and a state of the sleep study. The state of the sleep study indicates the position the sleep study is in in the process flow from being recorded to completed. Some examples of states include, without limitation, 'scoring', indicating that the sleep needs to be scored by the scoring technician, 'scored', indicating that the sleep study has been scored by the scoring technician, and 'reviewing', indicating that the scored sleep study data needs to be reviewed by a physician.

In an example of a process flow, sleep study data is first collected at sleep lab 2 and the raw sleep study data is uploaded to server 32. A lab manager then assigns the sleep study to a scoring technician which changes the state of the sleep study to 'scoring'. Once the scoring technician scores the sleep study, the sleep study state is changed to 'scored'. The lab manager then assigns the sleep study to a physician to review which changes the state of the sleep study to 'reviewing'. Once the physician completes the review of the sleep study, the state of the sleep study is changed to 'completed'.

When client 20 queries server 32, the query may only require one criteria to be met or multiple criteria to be met.

For example, client 20 may query server for all sleep studies assigned to a specified user or all sleep studies assigned to a specified user and having a specified state.

Once server 32 has been queried, any sleep studies meeting the predetermined criteria are indicated to client 20. At 44, client 20 determines if server 32 has indicated any sleep studies that meet the predetermined criteria. If not, client 20 proceeds to 40 and waits the predetermined time before querying the server 32 again. If client 20 determines that server 32 has indicated sleep studies meeting the predetermined criteria, client proceeds to 46.

At 46 client 20 checks if the sleep study files exist locally at 46 (e.g., client 20 checks whether the sleep study files are stored in the memory 22 corresponding to client 20). If the sleep study files do not exist locally, client 20 downloads all files corresponding to the sleep study at 48. Client 20 then returns to 40 and waits the predetermined time before querying the server 32 again.

If the sleep study files do exist locally, client 20 checks if any of the remotely stored sleep study files on server 32 are new or updated at 50. That is, client 20 checks if the local version of the sleep study files is the same as the version of the sleep study files stored on server 32. If client 20 determines that none of the remotely stored sleep study files are new or updated, client 20 returns to 40 and waits the predetermined time before querying the server 32 again. If client 20 determines that the remotely stored files on the server 32 includes new or updated files, client 20 proceeds to 52.

At 52, client 20 downloads any new or updated sleep study files from server 32. By only downloading new and updated files, downloading the entire sleep study can be avoided when only some of the sleep study files are new or updated. After downloading any new or updated sleep study files from server 32, client 20 returns to 40 and waits the predetermined time before querying the server 32 again.

The method of FIG. 2 may run on client 20 in any suitable manner such as, without limitation, as part of a software package or as a background process. The method of FIG. 2 may also run on client 20 as a background process that continues running even when a user is logged out of client 20. By periodically querying server 32 and automatically downloading sleep study data, sleep study data is automatically downloaded to client 20 without user interaction. Additionally, the criteria can indicate that a user will need to access the sleep study data in the near future. For example, when the sleep study is assigned to the scoring technician and has the 'scoring' state, the scoring technician will need to access the sleep study data in the near future. Rather than have the scoring technician manually initiate the download of the sleep study data and have to wait for the download to complete, client 20 can initiate the download of the sleep study data while the scoring technician is working on other matters or is out of the office. Thus, the sleep study data can be pre-downloaded to the client 20 and ready for the scoring technician when he is ready to access the sleep study data.

Figure 3:
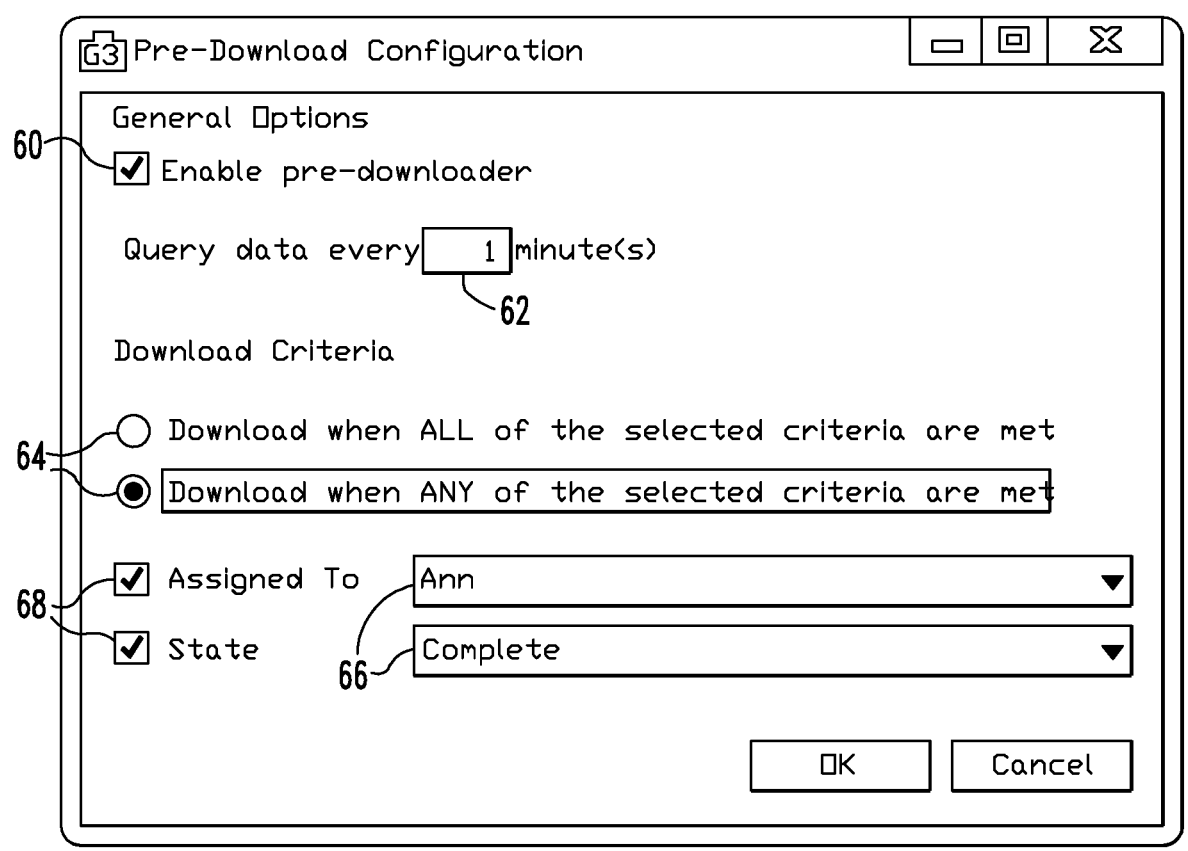
FIG. 3 is a view of a user interface for setting criteria for automatically downloading sleep study files according to one exemplary embodiment of the disclosed concept.

FIG. 3 is a view of a user interface for setting automatic sleep study download criteria in accordance with an embodiment of the disclosed concept. User interface includes an automatic download activation box 60. Automatic download activation box 60, when activated, enables client 20 to execute the method of FIG. 2. A predetermined time entry box 62 allows a user to enter the predetermined time client 20 waits before querying server 32. Selection buttons 64 allow a user to select whether one criteria or a plurality of criteria are used in the query to server 32.

To set values for criteria, user interface includes criteria value entry boxes 66. For example and without limitation, a user can enter the user the sleep study is assigned to and the state of the sleep study in the criteria value entry boxes 66. User interface also includes criteria activation boxes 68 which allow a user to select which criteria will be used in the query to server 32.

Although a few criteria have been shown and described herein, it will be appreciated by those having ordinary skill in the art that any suitable criteria may be used in the query to server 32 without departing from the scope of the disclosed concept.

Although the disclosed concept has been described in the context of transferring sleep study data, it is contemplated that the disclosed concept may also be adapted for use in transferring any type of data between remote locations and a central storage location. It will be appreciated that the disclosed concept is particularly suitable for use in transferring groups of files.

Furthermore, although the disclosed concept has been described in the context of automatically downloading files in a manner that would reduce wait time for a user, it is also contemplated that the disclosed concept may be advantageously applied to filter files that are downloaded to client 20. For example and without limitation, criteria can be used to determine which files are downloaded to client 20 and which are not. It is contemplated that the disclosed concept can be advantageously applied for use with, without limitation, music libraries, where the disclosed concept can be used to, for example, automatically download tracks from selected artists and/or albums. It is also contemplated that the disclosed concept can be advantageously used with, without limitation, document management systems, where the disclosed concept can be used, for example, to automatically download documents by a selected author.

The disclosed concept can also be embodied as computer readable codes on a tangible, non-transitory computer readable recording medium. The computer readable recording medium is any data storage device that can store data which can be thereafter read by a computer system. Non-limiting examples of the computer readable recording medium include read-only memory (ROM), non-volatile random-access memory (RAM), CD-ROMs, magnetic tapes, floppy disks, disk storage devices, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of automatically downloading data, the method comprising:
   with a client device, periodically querying a server for sets of data meeting predetermined criteria;
   receiving information on any sets of data meeting the predetermined criteria;
   for each set of data meeting the predetermined criteria, determining if the set of data exists or is up to date locally at the client device; and
   upon determining that a selected set of data does not exist or is not up to date locally at the client device, downloading at least a portion of the selected set of data from the server to the client device,
   wherein the set of data includes sleep study data,
   wherein the predetermined criteria include states of the sleep study, and
   wherein the states of the sleep study include scoring, scored, and reviewing.

2. The method of claim 1, wherein periodically querying the server comprises:
   waiting a predetermined time; and
   querying the server after waiting the predetermined time.

3. The method of claim 1, wherein upon determining that the selected set of data does not exist locally, downloading the entire selected set of data.

4. The method of claim 1, wherein upon determining that the selected set of data is not up to date locally, downloading any new or updated files in the selected set of data.

5. A non-transitory computer readable medium storing one or more programs, including instructions, which when executed by a computer, causes the computer to perform a method of automatically downloading data, the method comprising:
   with a client device, periodically querying a server for sets of data meeting predetermined criteria;
   receiving information on any sets of data meeting the predetermined criteria;
   for each set of data meeting the predetermined criteria, determining if the set of data exists or is up to date locally at the client device; and
   upon determining that a selected set of data does not exists or is not up to date locally at the client device, downloading at least a portion of the selected set of data from the server to the client device,
   wherein the set of data includes sleep study data,
   wherein the predetermined criteria include states of the sleep study, and
   wherein the states of the sleep study include scoring, scored, and reviewing.

6. The non-transitory computer readable medium of claim 5, wherein periodically querying the server comprises:
   waiting a predetermined time; and
   querying the server after waiting the predetermined time.

7. The non-transitory computer readable medium of claim 5, wherein upon determining that the selected set of data does not exist locally, downloading the entire selected set of data.

8. The non-transitory computer readable medium of claim 5, wherein upon determining that the selected set of data is not up to date locally, downloading any new or updated files in the selected set of data.

9. A system to automatically download data, the system comprising:
   a client device structured to periodically query a server for sets of data meeting predetermined criteria, to receive information on any sets of data meeting the predetermined criteria, and, for each set of data meeting the predetermined criteria, to determine if the set of data exists or is up to date locally at the client device for each set of data meeting the predetermined criteria,
   wherein the client device is structured to download at least a portion of the selected set of data from the server upon determining that the selected set of data does not exist or is not up to date locally at the client device,
   wherein the set of data includes sleep study data,
   wherein the criteria include states of the sleep study, and
   wherein the states of the sleep study include scoring, scored, and reviewing.

10. The system of claim 9, wherein the client device is structured to wait a predetermined time and to query the server after waiting the predetermined time.

11. The system of claim 9, wherein the client device is structured to download the entire selected set of data upon determining that the selected set of data does not exist locally.

12. The system of claim 9, wherein the client device is structured to download any new or updated files in the selected set of data upon determining that the selected set of data is not up to date locally.

13. The system of claim 9, wherein the predetermined criteria includes a user the sleep study is assigned to.

* * * * *